(12) United States Patent
Münchmeyer et al.

(10) Patent No.: US 8,742,363 B2
(45) Date of Patent: Jun. 3, 2014

(54) METHOD AND APPARATUS FOR IONIZING GASES USING UV RADIATION AND ELECTRONS AND IDENTIFYING SAID GASES

(75) Inventors: Wolf Münchmeyer, Ehra-Lessien (DE); Bert Ungethüm, Schwerin (DE); Andreas Walte, Schwerin (DE)

(73) Assignee: Airsense Analytics GmbH, Schwerin (DE)

( * ) Notice: Subject to any disclaimer, the term of this patent is extended or adjusted under 35 U.S.C. 154(b) by 0 days.

(21) Appl. No.: 13/820,654

(22) PCT Filed: Aug. 11, 2011

(86) PCT No.: PCT/EP2011/063807
§ 371 (c)(1),
(2), (4) Date: Mar. 4, 2013

(87) PCT Pub. No.: WO2012/031850
PCT Pub. Date: Mar. 15, 2012

(65) Prior Publication Data
US 2013/0153762 A1 Jun. 20, 2013

(30) Foreign Application Priority Data
Sep. 9, 2010 (EP) .................................. 10175936

(51) Int. Cl.
*H01J 49/14* (2006.01)
*H01J 49/10* (2006.01)
*H05H 1/00* (2006.01)

(52) U.S. Cl.
USPC ................... 250/423 P; 250/423 R; 250/424; 315/111.21; 315/111.81; 356/316

(58) Field of Classification Search
USPC .............. 250/423 P, 423 R, 424; 315/111.21, 315/111.81; 356/316
See application file for complete search history.

(56) References Cited

U.S. PATENT DOCUMENTS 3,621,240 A 11/1971 Cohen et al.
5,504,326 A * 4/1996 Reilly et al. .................. 250/282
(Continued)

FOREIGN PATENT DOCUMENTS

DE 19627621 1/1998
DE 19730896 1/1999
(Continued)

OTHER PUBLICATIONS

A.A. Shvartsburg: "Differential Ion Mobility Spectrometry", CRC Press, (2009).
(Continued)

*Primary Examiner* — David A Vanore
(74) *Attorney, Agent, or Firm* — Norris McLaughlin & Marcus, P.A.

(57) ABSTRACT

The invention relates to a method for ionizing and identifying gases, wherein the gases to be identified are ionized in a reaction chamber and the product ions are measured, wherein the measurement of the product ions takes place via electrical fields acting on the product ions and the detection is performed with a detector for ions. It is provided that ionization takes place via UV radiation, and that simultaneously or sequentially ionization by electrons takes place. The invention further relates to a device for ionizing and identifying gases, which includes an ion source chamber having an ion source and an ion mobility spectrometer. For this purpose, a partition between the ion source chamber and the ion mobility spectrometer has a UV-transparent window and a window permeable for electrons, wherein UV radiation and electron radiation can be generated in the ion source chamber with the ion source.

18 Claims, 2 Drawing Sheets

(56) References Cited

U.S. PATENT DOCUMENTS

Figure 1:
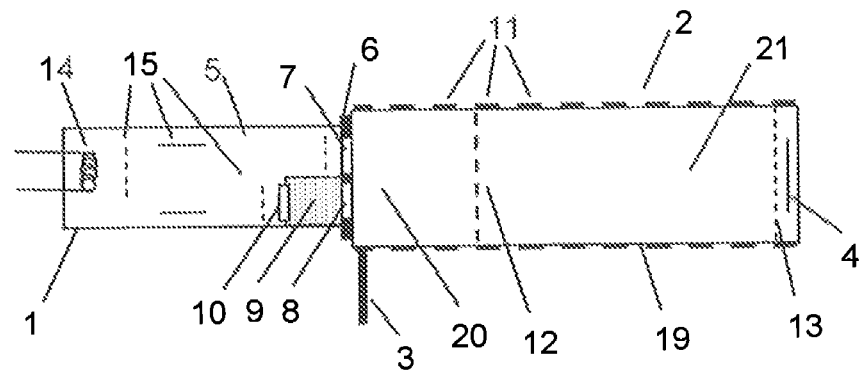

| | | | |
|---|---|---|---|
| 5,808,308 A * | 9/1998 | Holkeboer | 250/423 R |
| 5,969,349 A | 10/1999 | Budovich et al. | |
| 6,100,521 A | 8/2000 | Döring et al. | |
| 6,429,426 B1 * | 8/2002 | Doring | 250/288 |
| 6,509,562 B1 | 1/2003 | Yang et al. | |
| 6,646,257 B1 * | 11/2003 | Fischer et al. | 250/288 |
| 6,797,943 B2 * | 9/2004 | Losch et al. | 250/282 |
| 6,919,562 B1 * | 7/2005 | Whitehouse et al. | 250/288 |
| 7,034,291 B1 * | 4/2006 | Fischer et al. | 250/288 |
| 7,078,681 B2 * | 7/2006 | Fischer et al. | 250/288 |
| 7,315,020 B2 * | 1/2008 | Park et al. | 250/288 |
| 7,411,186 B2 * | 8/2008 | Mordehai | 250/288 |
| 7,417,224 B2 * | 8/2008 | Zimmermann et al. | 250/286 |
| 7,488,953 B2 * | 2/2009 | Fischer et al. | 250/425 |
| 7,642,510 B2 * | 1/2010 | McEwen | 250/288 |
| 8,080,783 B2 * | 12/2011 | Whitehouse et al. | 250/288 |
| 8,410,704 B1 * | 4/2013 | Cooley et al. | 315/111.21 |
| 8,431,889 B2 * | 4/2013 | Zimmermann et al. | 250/288 |
| 8,461,521 B2 * | 6/2013 | Vestal | 250/287 |
| 2002/0185594 A1 | 12/2002 | Doring | |
| 2006/0186330 A1 | 8/2006 | Zimmermann et al. | |
| 2007/0023637 A1 | 2/2007 | Ulrich et al. | |
| 2008/0296485 A1 * | 12/2008 | Benter et al. | 250/282 |
| 2010/0006751 A1 | 1/2010 | Bather et al. | |
| 2013/0153762 A1 * | 6/2013 | Munchmeyer et al. | 250/282 |

FOREIGN PATENT DOCUMENTS

| | | |
|---|---|---|
| DE | 10042394 | 4/2002 |
| DE | 101 20 335 A1 | 10/2002 |
| DE | 102005007746 | 8/2006 |
| DE | 102005028930 | 1/2007 |
| DE | 102008032333 | 6/2010 |
| EP | 2 006 672 A1 | 12/2008 |
| GB | 2 315 155 A | 1/1998 |
| JP | 2005 093152 A | 4/2005 |

OTHER PUBLICATIONS

F. Hasse: "Electron Permeable Membranes for MEMS electron sources" Sensors and Actuators A. Bd. 132, Seiten 98-103, 2006.

G.A. Eiceman and Z. Karpas "Ion Mobility Spectrometry" (2nd. edition, CRC, Boca Raton, 2005).

International Search Report Dated Oct. 28, 2011, Mailed Nov. 8, 2011.

* cited by examiner

METHOD AND APPARATUS FOR IONIZING GASES USING UV RADIATION AND ELECTRONS AND IDENTIFYING SAID GASES

This application is a 371 application of PCT/EP2011/063807 filed Aug. 11, 2011, which claims foreign priority benefit under 35 U.S.C. §119 of European Patent application 10175936.3 filed Sep. 9, 2010.

The invention relates to a method and a device for ionizing and identifying gases.

Such methods and the associated devices for detecting and identifying gases are used for detecting and identifying chemical substances or compounds, in particular of explosive and/or unhealthy substances or compounds to be detected at very low concentrations.

The detection of explosive and/or toxic chemical compounds requires measurement methods with detection limits in the ppt-ppb range. Spectrometers are therefore frequently used for detecting and identifying these chemical compounds. Preferably, ion mobility spectrometer (IMS), also referred to as plasma chromatographs, are used, wherein in contrast to other spectrometers, such as a mass spectrometer, the chemical substances are not detected in a vacuum and hence no vacuum pump for generating a vacuum is required. IMS have therefore a small footprint and an inexpensive construction compared to other spectrometers. Mass spectrometers are advantageous because their resolution and hence their selectivity is typically superior to that of the IMS.

A general overview of IMS and their applications can be found, for example, in: G. A. Eiceman and Z. Karpas "Ion Mobility Spectrometry" (2nd. edition, CRC, Boca Raton, 2005).

The structure and the operation of the IMS have been described in various publications.

For example, U.S. Pat. No. 3,621,240 discloses a classic time-of-flight IMS, which takes advantage of the different mobility of ions at atmospheric pressure. The target compounds are hereby continuously ionized in an ion source. Frequently, radioactive sources are used which ionize the air molecules directly. These ionized air molecules react further and form reactant ions in conjunction with water molecules. These reactant ions react with the compounds of interest via proton transfer reactions, electron transfer reactions or proton abstraction reactions and form the so-called product ions.

These product ions are introduced within a very short time span of about 200 microseconds by way of an electric grid into a drift tube, which has an electric field and accelerates the ions in a drift gas, typically filtered air at ambient pressure. By changing the polarity of the electric field of the drift region, positive ions can be detected in a positive operating mode and negative ions can be detected in a negative operating mode. The introduced product ions are continuously accelerated by the electric field and are continuously decelerated through collisions with the neutral molecules in the drift gas, producing an average drift velocity. The electric field exerts on all ions of identical charge the same pulling force. However, since the product ions have different masses and shapes, the product ions assume drift velocities in the electric field. The product ions strike a detector at the end of the drift tube at different times according to the different drift velocities. From the different times-of-flight of the product ions through the drift tube, which are typically in the range 5 to 30 milliseconds, conclusions can be drawn with respect to the different examined chemical compounds.

The switching process of the electric grid, which lets only a portion of the ions pass into the drift space, provides a starting pulse for the measurement of the drift velocity of the classical time-of-flight IMS. The introduced ion packet broadly diffuses during the time-of-flight. The signal measured at the detector is therefore in the shape of a Gaussian bell curve. The drift velocity can be determined from the measured time-of-flight or from the drift time at the maximum of the bell-shaped curve and the known length of the drift region, wherein a resulting spectrum can be used for identifying the chemical substances or compounds.

The time-of-flight of the product ions through the drift tube is inversely proportional to the drift velocity of the product ions striking the detector. The drift velocity, as a result of the acceleration in the electric field and the deceleration due to collisions of ions with the neutral molecules, depends in turn on the ion mass or the ion size and the ion shape, respectively.

In addition to the classic time-of-flight IMS systems, ion mobility spectrometers are known, where the ions are transported by a flow of air and are deflected perpendicular to the gas flow by electrostatic fields and are detected by using several electrodes. These IMS systems, also referred to as "Aspirating IMS", are described, for example, in a compact design by Bäther et al. (DE 10 2005 007 746 B4).

When using asymmetric alternating fields of high field strength oriented perpendicular to the gas flow and separating the ions based on the dependence of the mobility on the field strength, positive and negative ions can be transported simultaneously through two electrodes and detected by two additional electrodes disposed at the end of the arrangement. These IMS systems, also referred to as "Differential Mobility Spectrometer, DMS" or "Field Asymmetric Ion Mobility Spectrometer, FAIMS", are described in detail, for example, by A. A. Shvartsburg, "Differential Ion Mobility Spectrometry" (CRC Press, Boca Raton, 2009).

However, all these IMS disadvantageously use radioactive sources for ionization. Tritium, nickel-63, or americium-241 is typically used as radioactive materials. Radioactive ionization sources, however, can disadvantageously pose a hazard for the environment and the health of workers at the production and service facilities. The use and distribution of devices that include a radioactive source are subject to regulatory requirements that may be different from country to country.

These regulatory requirements are thus associated with very high administrative and financial requirements Therefore, attempts have been made to replace the radioactive ion sources. For example, ion sources which ionize in a gas discharges exist. A corona discharge is frequently used, which however operates with different ionization processes. In particular, for example, ozone and nitrogen oxides are produced when operating with air, which is often used as carrier and drift gas, which in turn frequently prevent the formation of product ions as a result of other ionization processes and/or chemical reactions. Gas discharges disadvantageously also increase the oxidation of the metallic surfaces in the IMS.

Attempts have therefore also been made since years to construct non-radioactive ionization sources that use the same ionization mechanisms and the same chemical reactions as the radioactive sources. The ionization with β-radiation, for example with Ni-63 or tritium, can be imitated, for example, directly by electron bombardment, and ionization with γ-radiation can be imitated directly with x-rays. The patent by Budovich et al. (DE 196 27 621 C2) describes an ion source wherein the electrons are generated in an evacuated source chamber by a non-radioactive electron source. The electrons are accelerated in an electric field, for example to 20 keV, and enter a reaction chamber at atmospheric pressure under partial deceleration through a window that is impermeable for gases and arranged in front of the source chamber.

Like with a radioactive source, the electrons ionize the gas in the reaction chamber. Mica was used as a window material. The patent by Döring (DE 101 20 335 C2) describes a similar structure wherein the electrons are decelerated in a thin membrane made of beryllium and having a metallic coating, and the generated x-rays are used for ionization.

Electron sources are also known which have windows made of silicon nitride that are permeable for electrons and impermeable for gases, and have thicknesses of less than 300 nanometers. Bäther et al. (DE 10 2005 028 930 A1) describe coupling of these ion sources with an ion mobility spectrometer. Other electron sources of this type which are produced employing production processes of the semiconductor industry are described by F. Haase et al. ("Electron permeable membranes for MEMS electron sources", Sensors and Actuators A, 132 (2006) 98-103) and S. Zimmerman et al. (DE 10 2008 032 333 A1).

These sources have the same ionization mechanisms as the radioactive sources and can be used as a substitute for radioactive sources. As with radioactive sources, the ionization of the target molecules occurs through charge transfer between the duster ions of the air, i.e. the reactant ions, and the analyte, wherein the reactant ions are not formed by alpha particles, beta particles or gamma rays, but instead by electrons or x-rays.

Like with radioactive sources, these sources are disadvantageously unable to detect some very toxic organic compounds, such as benzene, arsine or phosphine. Many organic molecules, such as alkanes and alkenes, or aromatics, such as toluene or chlorobenzene, are not detected due to their small proton affinities or their small electron affinities or due to their low electro negativities or because they have the same drift times as the duster ions. Another disadvantage is that the measurable concentration range has for many substances an upper limit and is linear only over a small range.

The ionization with photons represents another method for producing ions. The ionization with UV radiation is known and is used, for example, in photoionization detectors.

Photoionization enables the detection of molecules over a wide concentration range. In contrast to ionization with radioactive sources, the analytes are ionized by the photons directly. Typically, UV lamps with an ionization energy of 10.6 eV are used, causing all molecules with ionization potentials smaller or equal to this ionization energy to be ionized. As described in the patent by RAE Systems (U.S. Pat. No. 6,509,562 B2), molecules can be selectively ionized and detected by using different UV sources with different energies.

Disadvantageously, however, negative ions are rarely formed via photoionization, generally preventing for example the detection of halogenated hydrocarbons. Since the energy of the UV radiation is less than the ionization potentials of nitrogen and oxygen, no signal is generated in air. Disadvantageously, no reactant ion peak (RIP) is therefore present when ionizing with UV radiation, so that there is no peak for the internal calibration.

Some of the described disadvantages can be remedied by combining different ion sources. For example, the patent by Bensch et al. (DE 100 42 394 B4) describes a combination of a radioactive source and a UV lamp with a drift tube. Combinations of at least one radioactive source with additional ion sources and with different drift tubes are described, for example, by Döring et al. (DE 197 30 896 C2).

The disadvantage of these arrangements is that a radioactive source must still be used. Another disadvantage is that the radioactive sources cannot be easily turned off. Some compounds, such as benzene, which have the same drift times as the cluster ions in air, cannot be detected when using only a single drift tube with at least one radioactive source. Another disadvantage is that simultaneous detection of multiple toxic compounds is possible only when using different ion sources with different drift tubes, resulting in a complex design and high production costs of these systems.

It is therefore desirable to combine a non-radioactive ion source, that produces identical spectra by using electron bombardment or x-rays, and radioactive sources and alternatively also photoionization sources that produce identical spectra by UV radiation, with a separation and detection method. It would also be desirable to operate this non-radioactive ion source either alternatingly with electron radiation or with x-ray or with UV radiation.

It is therefore an object of the invention to develop a generic method for ionizing gases and an corresponding device which has a simple compact design and enables the ionization of gases at atmospheric pressure by electron bombardment or x-rays or UV radiation, respectively, wherein the ions are detected by using a separation method. According to the invention, the ion source is constructed so that particularly the ionization via electron bombardment can be quickly turned on and off.

Regarding the method, the object is attained by the features of claim 1 and regarding the device by the features of claim 10. Advantageous embodiments are recited in the dependent claims 2 to 9 and 11 to 18.

According to the invention, the ionization occurs by way of UV radiation, with ionization by way of electrons occurring simultaneously or sequentially.

The novel method for ionizing and identifying gases as well as a corresponding device eliminate the aforementioned disadvantages of the prior art.

With the novel method for ionizing and identifying gases, the ionization is advantageously non-radioactive, and the device also enables ionization by way of electrons as well as by way of UV radiation.

In a preferred embodiment of the invention, the ionization may occur with electrons by electrically accelerating the electrons in a low pressure region and thereafter further accelerating the electrons towards an electron window which is permeable for electrons, with the ions then being generated in a high-pressure region.

Moreover, in a preferred embodiment of the invention, the ionization may occur indirectly with electrons by electrically accelerating the electrons in a low pressure region and thereafter further accelerating the electrons towards an electron window, where the electrons are strongly decelerated to produce bremsstrahlung, which then generates ions in a high-pressure region.

Figure 2:
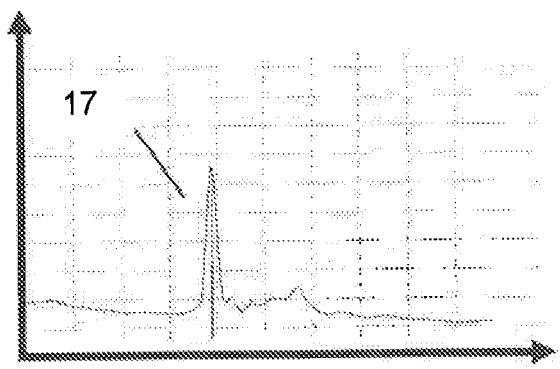
Figure 3:
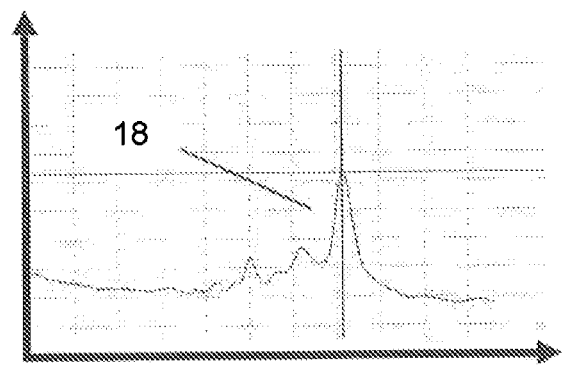
Figure 4:
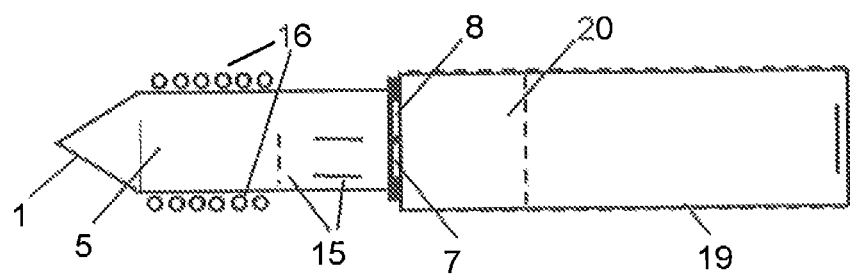
Figure 5:
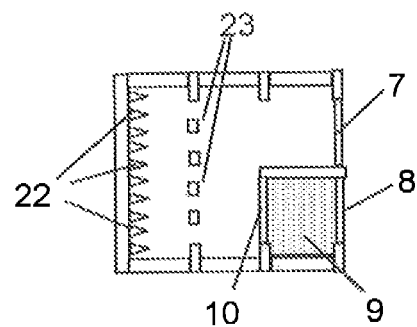
Figure 6:
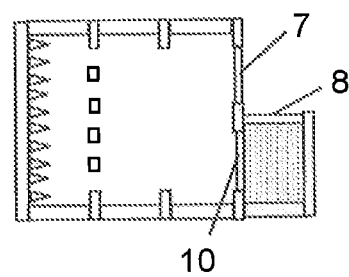

The novel method for ionizing and identifying gases as well as the corresponding device may be realized in various ways. These exemplary embodiments will be described in more detail with reference to the appended drawings, which show in:

FIG. 1 a schematic diagram of the novel ion source coupled to an ion mobility spectrometer;

FIG. 2 a spectrum from an ion mobility spectrometer of a measurement of hexane with a radioactive ion source (no product ions);

FIG. 3 a spectrum from an ion mobility spectrometer of a measurement of hexane with a UV ion source (clearly visible product ions);

FIG. 4 a schematic diagram of another variant of the novel ion source coupled to an ion mobility spectrometer;

FIG. 5 a schematic diagram of another miniaturized variant the novel ion source; and FIG. 6 an embodiment of a miniaturized variant of the novel ion source.

The device according to the invention for ionizing gases is composed in an exemplary embodiment according to FIG. 1 of an ion source 1 and an ion mobility spectrometer 2 which includes a drift tube 19, which is delimited, on one hand, by an inlet system 3 having an ion source 1 and, on the other hand, by a detector 4.

Drift electrodes 11 and an electric gate 12 are located in the drift tube 19, in the exemplary embodiment in the Bradbury-Nielsen geometry, whereby the interior space of the drift tube 19 is divided into a reaction chamber 20 and a drift chamber 21. A shielding grid 13 providing capacitive decoupling is located in front of the detector 4. The drift electrodes 11 are each electrically interconnected by resistors, thus forming DC electrodes. The voltages applied to the drift electrodes 11 are selected so as to produce a constant field strength in the drift tube 19.

The ion source 1 is composed of a vacuum-tight ion source chamber 5 which is separated from the reaction chamber 20 by a partition 6. The partition 6 includes a windows 7 that is permeable for electrons and impermeable for gas and may be made of an approximately 100 nm to 400 nm thin silicon nitride membrane or a diamond membrane, and a second window 8 transparent for UV radiation, which may be made of $MgF_2$.

The windows 7 may also be made of beryllium, particularly beryllium having a metallic coating.

In addition, a gas chamber 9 is disposed in the ion source chamber 5 wherein the gas chamber 9 is preferably filled with an inert gas at pressures greater than or equal to atmospheric pressure. This gas chamber 9 is also connected to the partition 6. Another window 10 permeable for electrons is located on the opposite side of the gas chamber 9.

The ion source chamber 5 of the arrangement in FIG. 1 is under a high vacuum. In this arrangement, the electrons are generated by a filament 14. The electrode arrangement 15 for accelerating and focusing the electrons is mounted so that the electrons are either directly incident on the window 7 after bypassing the gas chamber 9 and enter from there the reaction chamber 20, or are incident on the window 10, where the electrons enter the gas chamber 9 and produce through interaction with the gas UV radiation that can in turn enter the reaction chamber 20 through the UV-transparent window 8. The electrons are accelerated by high voltages in the range from 2 to 50 keV.

The electrons that are accelerated and pass through the thin window 7 will mainly ionize air molecules. Reactant ions 17 are formed through additional reactions and combination with water molecules. These reactant ions will subsequently ionize the molecules of the tested chemical compound via proton transfer, electron transfer or proton-abstraction reactions and form product ions. The ionization process proceeds very similar to the ionization process with radioactive sources, thus producing identical spectra.

The electrons that are accelerated and pass through the thin window 10 are decelerated in the gas in the gas chamber 9. Suitable gases are noble gases. The deceleration of the electrons in the inert gas produces light emission in the UV spectral range due to the excimer emission from the noble gases. Excimers are two-atomic molecules that only exist in the excited state. The excimer emission only occurs at pressures of about 0.2 bar and above, whereby higher pressures from about 1 bar to 3 bar are preferred. The UV spectrum of the excimer emission depends on the noble gas. Exchanging the inert gas then produces different light emissions, which may be in the wavelength range from 200 nm and below. The UV spectrum may be changed by energy transfer processes by admixing small amounts of a heavier inert gas.

By applying a deflection voltage to the electrode arrangement 15, the electrons may alternatingly enter the gas chamber for ionization with UV radiation or enter the reaction chamber 20 directly through the electron-permeable window 7.

With this arrangement, the ionization with the electrons can be turned on and off; the UV radiation can also be simultaneously turned on and off.

Thus, a quick changeover between electron radiation and the photon radiation, i.e. UV radiation, is possible within a matter of milliseconds.

The substances to be analyzed pass through the intake system 3, which may for example be composed of a thin silicon membrane, into the reaction chamber, where they are ionized either by electrons or by the UV radiation. The ions produced in the reaction chamber 20 are accelerated towards the electric gate 12 by electric field built up by the drift electrodes 11. The electric inlet grid, for example according to the Bradbury-Nielsen geometry, is composed of an alternating arrangement of electric conductors, with an electric field between the conductors preventing the ions from passing therethrough. The ions are temporarily attracted by the electric field in the drift space 21 when the voltage between the electrical conductors is switched off for a few microseconds. Only a portion of the ions thus passes into the drift space 21, where additional drift electrodes 11 guide the ions to the detector 4. The ions constantly collide with the neutral molecules in the drift gas while being transported in the electric field. The drift gas is generally composed of dry air and is conveyed via a pump in a direction opposite to the direction of flight of the ions. The time-of-flight of the ions depends inter aha on the collision cross-section of the ions, meaning that small ions arrive at the detector earlier than large ions. The intensity of the detector signal, i.e. the number of ions as a function of the time-of-flight, is referred to as IMS spectrum. The polarity of the electric field in the drift tube 19 can also be reversed, allowing positive and negative ions to be measured.

FIG. 2 shows an IMS spectrum of a benzene-containing mixture measured with ionization by electrons. The spectrum shows essentially only the reactant ion peak 17, i.e. only the water clusters. Benzene is not detected. The same mixture produces a completely different spectrum when ionized by UV-radiation, as shown in FIG. 3. A product ion is designated here with 18.

Another embodiment of the novel device for ionizing gases is illustrated in FIG. 4.

In contrast to the FIG. 1, the ion source chamber 5 is no longer a gas chamber; instead, a gas resides in the ion source chamber 5, preferably a noble gas, and preferably at a negative pressure in the region where the Paschen curve has a minimum, i.e. in the region of a few millibar. The ion source chamber is made of an electrically non-conductive material, for example glass. A gas discharge is ignited in the ion source chamber 5 by a high AC voltage on the radiofrequency electrodes 16 arranged on the ion source chamber 5, generating UV radiation. These UV rays can enter the reaction chamber 20 through the UV-transparent window 8. At least one electrode arrangement 15 for extracting the electrons from the gas discharge and for focusing the electrons onto the electron-permeable window 7 is arranged in the ion source chamber 5. The extracted electrons are accelerated by the electrode arrangement 15 and may enter the reaction chamber 20 through the electron-permeable window 7.

The same components as described with reference to FIG. 1 are disposed in the drift tube 19.

UV-radiation is generated in the ion source 1 by the gas discharge, which can ionize some of the analytes directly.

The ionization with the electrons can be turned on and off by switching the voltage on the electrode arrangement 15 for accelerating and focusing the electrons periodically on and off. In this way, the spectra generated with the UV radiation can be superimposed on spectra generated with the electron radiation.

It will be understood that additional arrangements for ionizing with UV radiation and with electrons are possible. For example, UV radiation can be produced using a high DC voltage instead of an alternating voltage. Only corresponding electrodes need to be introduced into the ion source chamber.

Additional embodiments of the device according to the invention for ionizing gases are illustrated in FIG. 5 and FIG. 6.

In contrast to the FIG. 1 and FIG. 4, the ion source 1 is constructed with methods used in the field of semiconductor technology and the electrons are generated not by a filament, but rather by an arrangement of several field emitter tips 22. The electrons are accelerated with a grid 23 and accelerated towards the electron-permeable window 7, from where they enter the reaction chamber. The grid 23 may also be placed directly on the window 7. The electrons that arrive also through the second window 10 in the shape of a wide beam may partially enter the gas chamber 9 where they can produce UV radiation, which enters the reaction chamber again through the UV-transparent window 8.

Other geometric arrangements of this source are possible, as shown in FIG. 6. For example, the UV-transparent window 8 and the electron-permeable window 7 may not be located in the same plane, but may be arranged at an angle, so that the same region in the reaction chamber is ionized. A circular arrangement is also feasible wherein, for example, one half shell is provided with a UV-transparent window and the other half-shell is provided with a window that is permeable for electrons.

Other arrangements are possible, for example, the electrons in FIG. 1, FIG. 4, FIG. 5 and FIG. 6 may be generated by using the photoelectric effect, i.e. the electrons are generated with an external light source by illuminating with the photons a surface made of a material having a low work function for electrons, which is positioned in the ion source 1. The electrons may also be generated by a gas discharge, for example by a hollow cathode gas discharge, from which they can be extracted with an electrode arrangement.

Instead of ionization with electrons entering the reaction chamber 20 through the thin window 7, ionization can also be performed by using x-rays, preferably low-energy x-rays. For this purpose, only the windows 7 and/or 10 need to be replaced with other windows that fully decelerate the electrons. This can be accomplished, for example, by using thicker or metal-coated windows. An increase of the accelerating voltage of the electrode arrangement 15 also causes x-rays to contribute to the ionization, in addition to the electrons.

The lifetime of the aforedescribed ion sources may be increased by using additional elements, such as a getter material disposed in the ion source chamber.

It is also conceivable to change or modify the noble gas by way of corresponding openings in the gas chamber 9, allowing the UV radiation and thus the ionization energies to be changed in order to optimize the ionization for the target substance.

It is also feasible to optimize the selectivity and detection limit of the measurement method by using an additional reactive gas or dopant gas, which is introduced into the reaction chamber 20. When ionization occurs via electron impact reactions, this reaction gas can affect chemical reactions, which are controlled for example by proton affinities for positive ions or electron negativities for negative ions, thereby changing the selectivity of the method. It is also known to improve the detection limit when using reactive gases in the ionization with UV radiation.

Furthermore, combinations of the ion mobility spectrometer with other sensors or detectors and/or with other methods for increasing the selectivity, for example particularly with an upstream gas chromatograph, are feasible.

The drawbacks of the conventional methods can be obviated with the aforedescribed invention, since no radioactive substances are needed, so that with this novel ion source both aromatics, such as benzene, toluene, chlorobenzene, and aliphatic compounds, and arsine or phosphine, as well as halogen compounds can be detected by using UV-ionization and additionally ionization with electrons or bremsstrahlung. Both types of ionization can also be switched on and off, enabling detection of a much larger number of compounds and an improved identification through comparison of the determined spectra.

The use of non-radioactive sources has the additional advantage that the electron flow in the reaction chamber can be greater than that of a radioactive source, because the upper limit of the activity of the latter is restricted by regulatory requirements. As a result, significantly lower detection limits are possible with the novel ion source.

To improve the detection limit, several ion sources may be coupled with a detector, which is particularly advantageous in miniaturized embodiments.

It will be understood that the aforedescribed ion sources can also be coupled with other types of spectrometers. These include other IMS designs, such as "Differential Mobility" spectrometers, as well as mass spectrometers, such as the "Time-of-Flight (TOF)", quadrupole and ion trap mass spectrometers. In particular when coupling the aforedescribed ion sources with mass spectrometers, this ion source can be installed in high-pressure regions of the inlet, so that improved detection limits can be attained by incorporating an alternating ionization with UV radiation and electron impact.

LIST OF REFERENCE SYMBOLS

1 Ion source
2 Ion mobility spectrometer
3 Inlet system
4 Detector
5 Ion source chamber
6 Partition
7 Electron window
8 UV radiation transparent window
9 Gas chamber
10 Second electron window
11 Drift electrodes
12 Electric gate
13 Shielding grid
14 Filament
15 Electrode arrangement
16 Radio frequency electrodes
17 Reactant ion
18 Product ion
19 Drift tube
20 Reaction chamber 21 Drift space
22 Field emission tips
23 Acceleration grid

The invention claimed is:

1. A method for identifying and ionizing gases, wherein the gases to be identified are ionized in a reaction chamber and the product ions are measured, wherein the measurement of the product ions takes place by exposing the product ions to electric fields and the detection is performed with a detector for ions, wherein the ionization is performed using UV radiation, and that simultaneously or sequentially an ionization with electrons is performed.

2. The method according to claim 1, wherein the ionization is performed by accelerating the electrons electrically in a low pressure region and accelerating the electrons towards an electron window which is permeable for electrons, wherein the electrons penetrate the electron window and then generate ions in a high pressure region.

3. The method according to claim 2, wherein the UV radiation is generated with a gas discharge and that the electrons are extracted from the gas discharge by an electrode arrangement and focused onto the electron window.

4. The method according to claim 2, wherein the ionization with electrons occurs discontinuously during the ionization with UV radiation by guiding the electrons onto the electron window only for specified times.

5. The method according to claim 1, wherein the ionization is performed indirectly by accelerating the electrons electrically in a low pressure region and accelerating the electrons towards an electron window, where the electrons are strongly decelerated and produce bremsstrahlung, that is then used to produce ions in a high pressure region.

6. The method according to claim 1, wherein the electrons from an electron source, which is made of a filament or from one or more field emission tips, are
   a) accelerated towards a first electron window, penetrate the first electron window and/or generate bremsstrahlung, thereby ionizing molecules in the reaction chamber, and
   b) are subsequently accelerated towards a second electron window, penetrate the second electron window and generate, in a gas chamber, UV radiation, with the UV radiation passing through a UV-transparent window and ionizing molecules in the reaction chamber.

7. The method according to claim 6, wherein the ionization with UV radiation and by electron bombardment occurs discontinuously, in that
   a) the electrons are guided to the first electron window and thus generate ions in the reaction chamber, and
   b) thereafter the electrons are guided only for specified times onto the second electron window and these electrons produce, in the gas chamber, UV radiation through interaction with gases residing in the gas chamber, wherein the UV radiation then enters the reaction chamber through the UV-transparent window, so that ionization takes place by electron bombardment or with UV radiation, wherein with a first ionization type of the two ionization types ionization takes place continuously, whereas the second ionization type of the two ionization types is additionally briefly switched on.

8. The method according to claim 7, wherein, for identifying the substances, a spectra measured by ionization with UV radiation and a spectra measured by ionization with electron bombardment are considered in combination and the substances are identified using methods using database comparison.

9. The method according to claim 1, wherein ionization with UV radiation and by electron bombardment occurs discontinuously and alternatingly within a few milliseconds.

10. A device for ionizing and identifying gases, comprising an ion source chamber, having an ion source, and an ion mobility spectrometer, wherein a partition between the ion source chamber and the ion mobility spectrometer has a first window transparent to UV radiation and a second window permeable for electrons, wherein UV radiation and electron radiation can be generated by the ion source in the ion source chamber.

11. The device according to claim 10, wherein a noble gas resides in the ion source chamber under optimum pressure for a gas discharge, in a millibar range, and that the first window is made of magnesium fluoride or calcium fluoride, transparent to the UV radiation generated by the gas discharge, delimits the ion source chamber with respect to a reaction chamber, and the second window, permeable for electrons and made of silicon-nitride, diamond or beryllium, is located next to the first window that is transparent for UV radiation, and that electrodes for accelerating and focusing the electrons from the gas discharge onto the second window are arranged in the ion source chamber.

12. The device according to claim 11, wherein the ion source chamber is coupled with the reaction chamber of the ion mobility spectrometer.

13. The device according to claim 12, wherein the ion source chamber is coupled with the reaction chamber or with an inlet region of a mass spectrometer.

14. The device according to claim 10, wherein a high vacuum is present in the ion source chamber, at a pressure of less than $10^{-6}$ millibar, that the ion source chamber is delimited by the second window and a third window, that is permeable for electrons, whereby the second window is directly adjacent to the reaction chamber and the third window is adjacent to a gas chamber, where a noble gas at a pressure greater than 0.1 bar resides, and that the gas chamber abuts the reaction chamber with the first window that is transparent to UV radiation.

15. The device according to claim 14, wherein an electrode arrangement is disposed in the ion source chamber, wherein the electrode arrangement accelerates the electrons and transports the electrons towards the second and third windows or deflects the electrons from the second and third windows.

16. The device according to claim 10, wherein the second window decelerates electrons, is transparent for bremsstrahlung and is made of metal-coated beryllium.

17. The device according to claim 10, wherein an electron source, comprising a material having a low work function for electrons, is disposed in the ion source chamber and that one or more external light sources are positioned on the ion source chamber, which produce photons that release electrons at the electron source by way of the photoelectric effect.

18. The device according to claim 10, wherein the first window is not arranged in a plane with the second window and that the first and second windows are arranged such that the UV radiation and the electrons and/or the bremsstrahlung is intersectable in the reaction chamber.

* * * * *